United States Patent [19]

Suga

[11] Patent Number: 4,799,379
[45] Date of Patent: Jan. 24, 1989

[54] APPARATUS FOR MEASURING THE MOISTURE CONTENT OF SNOW PARTICLES

[75] Inventor: Nagaichi Suga, Tokyo

[73] Assignee: Suga Test Instrumenets Co., Ltd., Tokyo, Japan

[21] Appl. No.: 136,634

[22] Filed: Dec. 22, 1987

[30] Foreign Application Priority Data

Dec. 24, 1986 [JP] Japan .................. 61-310437

[51] Int. Cl.$^4$ .................. G01W 1/14
[52] U.S. Cl. .................. 73/76; 73/171
[58] Field of Search .................. 73/73, 76, 171

[56] References Cited

U.S. PATENT DOCUMENTS

| | | | |
|---|---|---|---|
| 417,357 | 12/1889 | Fergusson | 73/171 |
| 3,016,737 | 1/1962 | Todnem | 73/76 |
| 3,229,519 | 1/1966 | Nilsson | 73/171 |
| 3,472,088 | 10/1969 | Ojard | 73/171 |
| 4,150,570 | 4/1979 | Fuller | 73/73 X |
| 4,338,033 | 7/1982 | Kato et al. | 346/33 A X |

FOREIGN PATENT DOCUMENTS 2595473 1/1987 France .................. 73/171

Primary Examiner—Daniel M. Yasich
Attorney, Agent, or Firm—Wenderoth, Lind & Ponack

[57] ABSTRACT

An apparatus for measuring the moisture content of falling snow has a sheet of water-absorbing material containing a material which generates a color upon having water added thereto and which is movable from a snow receiving position to a first observation position and then to a heating position and then to a second observation position. A first light receiving sensor in said first observation position is directed toward the surface of the sheet for measuring the area of color formed by absorption of moisture from snow particles received on the sheet when the sheet is in the snow receiving position, a heater is positioned at the heating position for heating the sheet to melt the snow particles thereon, a second light receiving sensor in the second observation position is directed toward the surface of the sheet for measuring the area of color formed by the melted snow particles, and a processor is connected to the light receiving sensors for calculating the ratio of the measured areas as a measurement of the moisture content of the snow particles.

8 Claims, 2 Drawing Sheets

APPARATUS FOR MEASURING THE MOISTURE CONTENT OF SNOW PARTICLES

BACKGROUND OF THE INVENTION

This invention relates to an apparatus for measuring the moisture content of snow particles, and more particularly to such an apparatus which can continuously measure the moisture content of snow particles as they are falling.

Conventionally, an apparatus which can measure the moisture content of snow particles as they fall has not been available. However, measurement of the moisture content of snow that has fallen has been available and the technique for its use is generally as follows.

A predetermined quantity and weight of snow is taken out of fallen snow that has accumulated and it is melted by heating it. After the temperature of the melted snow is raised to a predetermined temperature, the calories required for such a temperature rise is determined. The thus determined value is called $Q_1$.

On the other hand, the same weight of snow having a moisture content of 0% at 0° C. is melted in the same way as above, and the calories required to raise the temperature of the melted snow to the same temperature as above is determined. The thus determined value is called $Q_2$.

In comparison with the snow with the value $Q_2$, the snow having the measured value $Q_1$ contains water and is wetted, so that the portion of the weight constituted by the water contained in the snow does not require the heat of fusion to melt it.

Therefore, the value of $Q_1$ is smaller than the value of $Q_2$, and the moisture content of the snow that has fallen is determined by this comparison.

In accordance with the prior art technique described above, however, it is only possible to determine the moisture content of the snow after it has fallen and has accumulated, but it is not possible to continuously determine the moisture content of the snow particles as they are falling.

In the industrial fields, artificial snowfall and snow deposition experiments have become necessary and artificial snow generating apparatuses have been developed to cope with such demands. When various experiments and studies are conducted with the snow from such artificial snow generating apparatuses, it is necessary to obtain snow having a desired moisture content by controlling in advance the quality of snow. Hence the development of an apparatus which can continuously measure the moisture content of the snow as it is falling has been in demand.

SUMMARY OF THE INVENTION

In order to satisfy the foregoing demand, the present invention provides an apparatus for measuring the moisture content of snow particles which can continuously calculate and measure the moisture content of the sampled falling snow particles by absorbing the water attached to the snow particles on a water-absorbing material containing a material that generates a color upon addition of water, the absorption of the water generating the color, measuring the area of the colored portion, heating and melting the snow particles, measuring the area of the colored portion formed by the melted snow particles, and then analyzing the two measured values to continuously indicate the moisture content of the snow particles.

More specifically, according to the present invention, a measuring apparatus is provided into which a trace amount of snow particles is continuously sampled from the falling snow. A sheet of water-absorbing material is provided therein which contains a material that generates a color upon addition of water, so that the moisture attached to the snow particles is absorbed by the material and the color is generated. A light receiving sensor is provided which measures the area of the colored portion on the material, and heating means is provided which, while the material is moved sequentially, heats and melts the snow remaining in the particle state on the material so as to turn it fully into water, and the thus melted snow is absorbed by the material and the color is again generated. Another light receiving sensor is provided which measures the area of this last generated colored portion. A microprocessor calculates the ratio of the areas of the two colored portions continuously, which gives a measure of the moisture content of the falling snow particles.

According to the construction described above, the falling snow particles that are sampled drop onto the water-absorbing material. Since the water-absorbing material contains the material that generated a color upon addition of water thereto, the water content of the snow particles is absorbed immediately and a color is generated. The area of this colored portion is measured optically by the light receiving sensor and this measured value is designated A.

Next, the water-absorbing material is moved and the snow particles remaining on the material under the particle state are heated and melted and the water thus generated is further absorbed by the material to generate the color. The area of this colored portion is measured optically by the other light receiving sensor and this measured value is designed B. These measured values A and B are analyzed by the processor and the moisture content (A/B) of the snow particles is calculated continuously.

DESCRIPTION OF THE PREFERRED EMBODIMENTS

Some preferred embodiments of the present invention will be described in detail with reference to the accompanying drawings.

Figure 1:
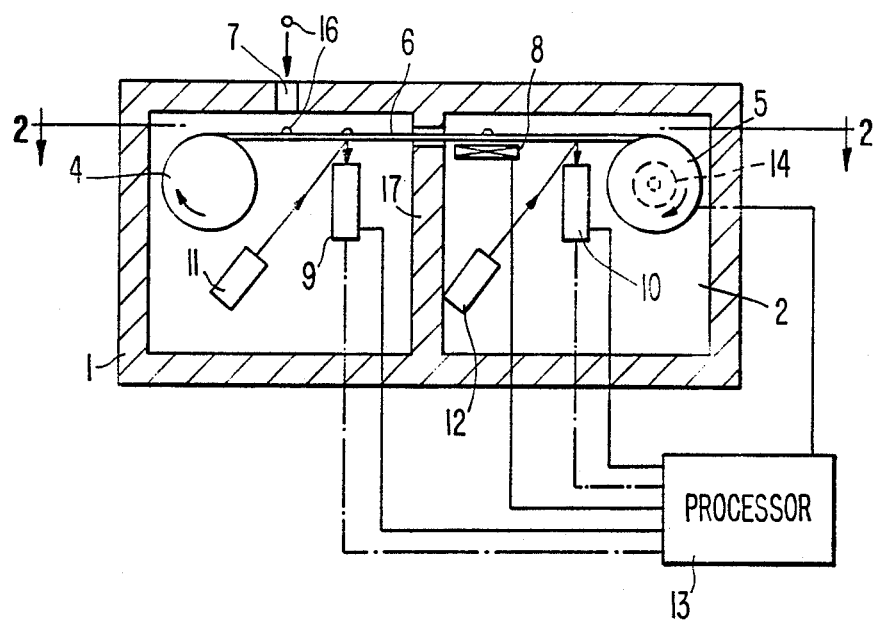
FIG. 1 is a longitudinal sectional elevation view of the apparatus of the present invention.
Figure 2:
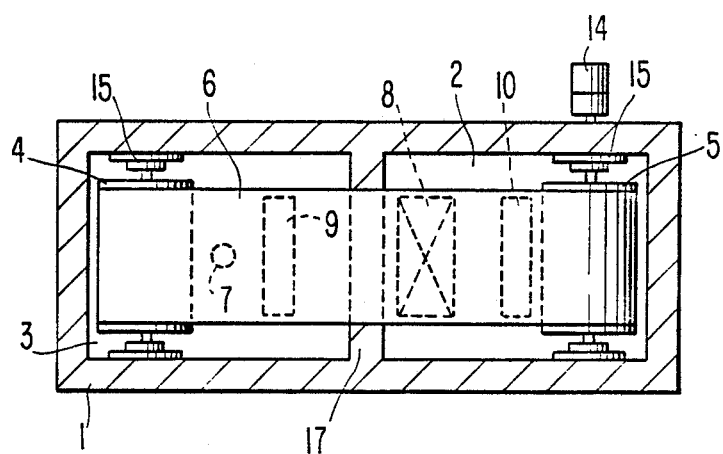
FIG. 2 is a longitudinal sectional plan view of the apparatus of FIG. 1 taken on line 2—2 of FIG. 1.

In the embodiment of FIGS. 1 and 2, the main body 1 of the measuring apparatus is divided adiabatically into a sampling chamber 3 and a melting chamber 2. A supply roller 4 is rotatably mounted in the sampling chamber 3 and a driven roller 5 is rotatably mounted in the melting chamber 2, the rollers being mounted bearings 15. The driven roller 5 is rotated by a driving motor 14.

A sheet of water-absorbing material is in the form of a web 6 supplied from the roller 4 to the roller 5 and can be moved either continuously or intermittently by controlling the motor 14.

This water-absorbing material is composed, for example, of filter paper containing among the fibers thereof a coloring material such as so-called "water-blue" particles, which generate a blue color upon reaction with water, as a material that generates a color upon addition of water.

This coloring material may be a material other than the "water-blue" particles described above, so long as it generates a color upon reaction with water and the resulting colored area can be measured optically. Moreover, the water-absorbing material of the web may be composed of material other than the filter paper described above.

An intake port 7 for the snow particles 16 opens into the top of the sampling chamber 3 to a snow receiving position, and a trace amount of snow particles 16 can fall therethrough onto the web 6 of water-absorbing material and is collected thereon.

A light receiving sensor 9 is disposed beneath the web 6 of water-absorbing material at a first observation position toward the melting chamber 2 from the intake port 7 of the sampling chamber 3. After the moisture contained in the snow particles 16 which have fallen onto the web 6 of water-absorbing material is absorbed by the water-absorbing material and areas of blue color is generated, this light receiving sensor 9 measures the areas of colored portions of the web and sends a signal corresponding to the measured value to a processor 13.

A light projector 11 is disposed inside the sampling chamber 3 and projects rays of light onto the areas of blue color in order to facilitate the measurement by the light receiving sensor 9 and to obtain a more accurate measurement.

The driving motor 14 serves for driving the roller 5 to wind up the web 6 of water-absorbing material. It is actuated after the sensor 9 has measured the colored areas generated by the moisture contained in the snow particles, and carries the snow particles from which the water has been absorbed and which remain in the particle state and having a zero water content, into the melting chamber 2.

A heater 8 is disposed beneath the web 6 of water-absorbing material at a heating position, which is at the side of the melting chamber 2 which is toward the sampling chamber 3, and this acts to heat and melt the snow particles 16 carried by the web 6. Therefore, the snow particles 16 are changed completely to water and generate a larger size colored areas on the web 6 of water-absorbing material.

A further light receiving sensor 10 is disposed at a second observation position downstream, in the direction of web movement, of the heater 8 in the melting chamber 2 for measuring the areas of the colored portion of the web 6 produced by the melted snow particles 16 that are absorbed by the water-absorbing material, and sends a signal corresponding to the measured value to the processor 13.

A further light projector 12 is disposed inside the melting chamber 2 for projecting rays of light onto the web to facilitate the measurement by the light receiving sensor 10 to obtain a more accurate measurement.

The processor 13 includes a synchronization circuit connected to the light sensors 9 and 10, heater 8, and motor 14 for timing the operation of the two light receiving sensors 9 and 10 so as to be in synchronism with the feed speed of the rollers 4 and 5 and with the operation of the heater 8, in order to make sure that the same particles, the colored areas from the moisture of which are measured in the sampling chamber 3, are then melted in the melting chamber 2 and the colored areas produced thereby are measured.

The snow particles 16 sampled from the intake port 7 do not always drop one by one onto the web 6, but at times a plurality of particles fall onto the belt. The sensors 9 and 10 can measure a single area or the sum of a plurality of areas, so that the overall moisture content of the snow particles 16 can be calculated without any problem.

In the embodiment shown in FIGS. 1 and 2, the snow particles are moved linearly by use of the web 6 extending between the rollers 4 and 5, but the same measured values can be obtained by shaping the web of water-absorbing material in a disc-like form.

Figure 3:
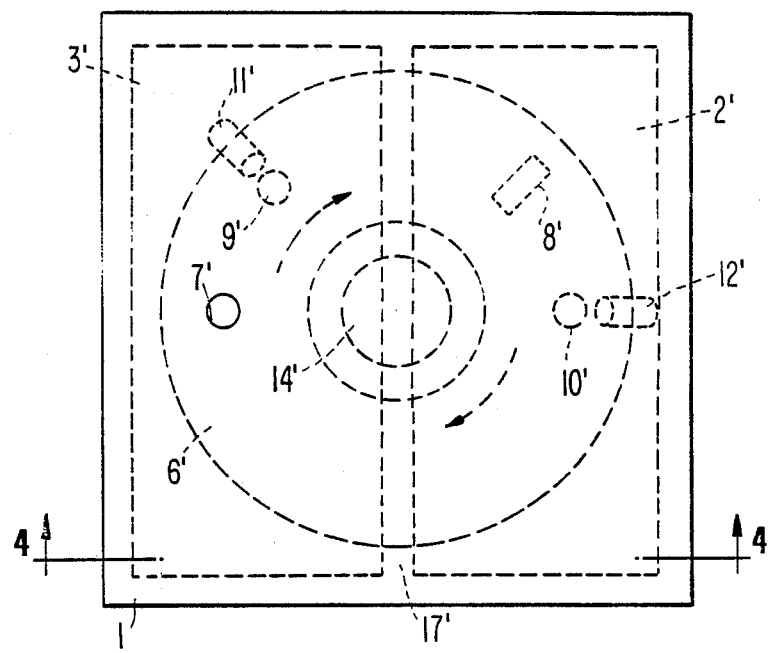
FIG. 3 is a plan view showing another embodiment of the apparatus of the present invention.
Figure 4:
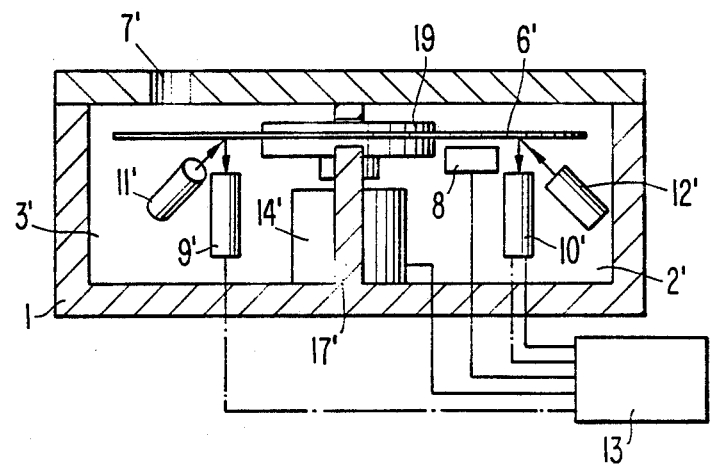
FIG. 4 is a longitudinal sectional view taken on line 4—4 of FIG. 3.

FIGS. 3 and 4 show another embodiment of the present invention, wherein the sheet of water-absorbing material is in the form of a disc-like element 6' and is rotatable. It is held between a pair of disc supports 18 and 19 mounted on a vertically oriented shaft of motor 14' so as to be rotatable through side by side sampling chamber 3' and melting chamber 2+ separated by partition 17'. The sampling chamber has an intake port 7' and the respective chambers have light receiving sensors 9' and 10' and light projectors 11' and 12' and directed toward the under side of the disc 6', and melting chamber has a heater 8' beneath the disc 6' at the position where it moves into chamber 2'. A processor 13 the same as the processor in FIGS. 1 and 2 is connected to the sensors 9' and 10', the heater 8' and the motor 14' as in the embodiment of FIGS. 1 and 2.

The snow particles that fall from the intake port 7' in the top wall of the main body 1' fall on the disc 6' and the water therein generates colored areas as it is absorbed by the color generating material in the water-absorbing material in the disc.

Next, the disc 6' of water-absorbing material is rotated clockwise by 45° by the driving motor 14' and the areas of the colored portions are lighted by light projector 11' and measured by the light receiving sensor 9' inside the sampling chamber 3, and a signal corresponding to the measured value is sent to the processor 13.

After the measurement of the first colored areas the disc 6' water-absorbing material is further rotated clockwise in two 45° movements or one 90° movement, so as to move the snow particles 16 the water content of which has been absorbed and the moisture content of which is zero and which remain in particle form into the melting chamber 2. The snow particles 16 are then heated and melted by the heater 8' and turned fully to water, forming larger colored areas on the disc 6' of water-absorbing material.

The disc 6' of water-absorbing material 6 is then rotated further clockwise by 45° and the colored areas are illuminated by the light projector 12' and measured the light receiving sensor 10'. A signal corresponding to the measured value is sent to the processor 13 for use in calculating the moisture content of the snow particles.

The procedures described above are repeated sequentially and the measurement of the moisture content of the snow particles can be made continuously.

The angle of rotation of the disc 6' of water-absorbing material can be change suitably whenever necessary.

By the apparatus of the present invention, it is possible to measure continuously the water content of the falling snow particles and to determine easily the quality of falling snow.

When various snowfall experiments and snow deposition experiments are to be conducted using snow generating by an artificial snow generating apparatus, the apparatus of the present invention can measure in advance the snow quality of the falling generated snow and be used as a basis for control of the snow quality of the artificial snow to obtain a desired snow quality.

What is claimed is:

1. An apparatus for measuring the moisture content of falling snow, comprising:
    a sheet of water-absorbing material containing a material which generates a color upon having water added thereto;
    means for moving said sheet from a snow receiving position to a first observation position and then to a heating position and then to a second observation position;
    a first light receiving sensor in said first observation position and directed toward the surface of said sheet for measuring the area of color formed by absorption of moisture from snow particles received on the sheet when the sheet is in the snow receiving position;
    a heater means at said heating position for heating said sheet to melt the snow particles thereon;
    a second light receiving sensor in said second observation position and directed toward the surface of said sheet for measuring the area of color formed by the melted snow particles; and
    calculating means connected to said light receiving sensors for calculating the ratio of the measured areas as a measurement of the moisture content of the snow particles.

2. An apparatus as claimed in claim 1 further comprising a light projector at each observation position for directing light onto the sheet for illuminating the colored areas.

3. An apparatus as claimed in claim 1 in which said sheet is an elongated web, and said means for moving said sheet comprises a supply roller from which said web is supplied and a driven roller to which said web extends from said supply roller past said positions, and a motor connected to said driven roller for rotating said driven roller to take up said web.

4. An apparatus as claimed in claim 3 in which said apparatus further comprises a body having side by side sampling and melting chambers and a partition separating said chambers, said sampling chamber having said snow receiving position and said first observation position therein with said web extending past said positions in the recited order, said sampling chamber having an intake opening at said snow receiving position and having said first light receiving sensor therein at said first observation position, and said melting chamber having said heating position and said second observation position therein with said web extending past said positions in the recited order, said partition having an aperture therein through which said web passes.

5. An apparatus as claimed in claim 4 in which said first and second light receiving sensors and said heater means are beneath said web.

6. An apparatus as claimed in claim 1 in which said sheet means is a disc, and said means for moving said sheet comprises a motor having a vertically oriented shaft on which said disc is mounted, said positions being spaced around said motor.

7. An apparatus as claimed in claim 6 in which said apparatus further comprises a body having side by side sampling and melting chambers and a partition separating said chambers, said sampling chamber having said snow receiving position and said first observation position therein with said disc being rotatable past said positions in the recited order, said sampling chamber having an intake opening at said snow receiving position and having said first light receiving sensor therein at said first observation position, and said melting chamber having said heating position and said second observation position therein with said disc being rotatable past said positions in the recited order, said partition having a slit therein in which said disc is positioned for rotation through the respective chambers.

8. An apparatus as claimed in claim 7 in which said first and second light receiving sensors and said heater means are beneath said disc.

* * * * *